US006232331B1

(12) United States Patent
Sankaranarayanan (10) Patent No.: US 6,232,331 B1
(45) Date of Patent: May 15, 2001

(54) BENZOFUROXAN DERIVATIVES, THEIR THERAPEUTIC USES AND PHARMACEUTICAL COMPOSITIONS

(75) Inventor: Alangudi Sankaranarayanan, Ahmedabad (IN)

(73) Assignee: Torrent Pharmaceutical Ltd., Gujarat (IN)

( * ) Notice: Subject to any disclaimer, the term of this patent is extended or adjusted under 35 U.S.C. 154(b) by 0 days.

(21) Appl. No.: 09/690,805

(22) Filed: Oct. 18, 2000

Related U.S. Application Data

(63) Continuation of application No. PCT/IB99/00893, filed on May 17, 1999.

(30) Foreign Application Priority Data

May 22, 1998 (IN) ............................................. 935/CAL/98

(51) Int. Cl.$^7$ ................................................. A61K 31/41
(52) U.S. Cl. ......................................................... 514/361
(58) Field of Search ............................................ 514/361

(56) References Cited

U.S. PATENT DOCUMENTS

| 5,272,164 | 12/1993 | Izawa et al. | 514/357 |
| 5,424,326 | 6/1995 | Schonafinger et al. | 514/364 |

FOREIGN PATENT DOCUMENTS

| 431 944A2 | 6/1991 | (EP) | C07D/271/12 |
| 574 726 A1 | 12/1993 | (EP) | C07D/498/04 |
| 98/35950 | 8/1998 | (WO) | C07D/285/14 |

OTHER PUBLICATIONS

Zhang, Cui L. et al, European Journal of Pharmacology, 252 (1994), pp. 299–304.
Ignarro, Louis, J., FASEB J. 1989 Jan.;3(1):31–36.
Benedini, F., et al., Journal of Medicinal Chemistry, 1995; 38:130–136.
Boulton, A.J. et al., Journal Chemical Society (C) 1966; 971–976, 1966.
Boulton, A.J. et al., Journal Chemical Society (B) 1967; 914–19.
Frampton, J. et al., Drugs 1992; 44(4) 625–55.
Furchgott, R. F. et al., Nature 1980; 288:373–76.
Gasco, A. et al., Liebigs Ann. Chem. 1973; 10:587–90.
Ghosh, P. B. et al., Journal of Medical Chemistry 1974; 17(2):203–206.
Ghosh, P. B. et al., Journal of Medicinal Chemistry 1972; 15(3):255–260.
Ghosh, P. B. et al., Journal of Medicinal Chemistry 1968; 11:305–311.
Henderson, A. H., Br. Heart J., 1991; 65:116–125.
Wessel, David L., Advances in Pharmacology 1995; 34:475–504.

Nishikawa et al., Journal Pharmacol. Exp. Ther., 1982 200; 183–190.
Needleman, P. et al., Journal Pharmacol. Exp. Ther. 1973; 184:709–715.
Mongada, S. et al., The New England Journal of Medicine 1993; 329(27):2002–2012.
Vane, J. R. et al., The New England Journal of Medicine 1990:323:27–36.
The Merck Manual of Diagnosis and Therapy (16$^{th}$ Edition 1992) pp. 498–505.
Martindale The Extra Pharmacopoeia (30$^{th}$ Edition 1993) pp. 1019–1026.
The Essential Guide to Prescription Drugs 1994 edited by James W. Long and James J. Raybacki pp. 42–46.
Harrison's Principles of Internal Medicine (13$^{th}$ Edition, 1994) pp. 1077–1084.
Goodman and Gilman's The Pharmacological Basis of Therapeutics (9$^{th}$ Edition 1996) pp. 759–767.
Zhang W. et al., Chemical Abstracts, Columbus, Ohio U.S., vol. 125, No. 1, Jul. 1 1996, p. 1182.
Copy of International Search Report for PCT/IB99/00893 (1999).

Primary Examiner—Raymond Henley, III
(74) Attorney, Agent, or Firm—Sughrue, Mion, Zinn, Macpeak & Seas, PLLC (57) ABSTRACT

The invention discloses use of a compound of the benzofuroxan series for treatment of cardiovascular disorders represented by the general formula (I)

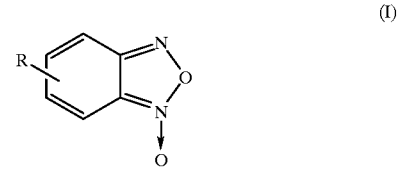

(I)

and pharmaceutically acceptable salts thereof wherein:
  R is halogen, acetoxy, —X—R', —C(O)NR"R'", or —C(O)Cl;
  X is oxygen, sulfur, —C(O)—, or —C(O)O—;
  R' is hydrogen, straight chain or branched lower alkyl ($C_1$–$C_8$);
  R" and R'" are independently hydrogen, straight chain or branched lower alkyl ($C_1$–$C_8$) or R" and R'" are linked together with or without a heteroatom selected from the group consisting of oxygen and nitrogen wherein substitution on nitrogen is with hydrogen or lower alkyl.

The invention further discloses pharmaceutical compositions containing compounds of general formula I as active ingredients.

The invention also discloses a method of treatment of mammal, including man, of coronary heart disease by administration of an effective amount of a compound of formula I as defined above.

19 Claims, 2 Drawing Sheets

BENZOFUROXAN DERIVATIVES, THEIR THERAPEUTIC USES AND PHARMACEUTICAL COMPOSITIONS

This is a continuation application of international application No. PCT/IB99/00893 filed May 17, 1999, the disclosure of which is incorporated herein by reference.

BACKGROUND OF THE INVENTION

1. Field of the Invention

This invention relates to the use of the compounds of benzofuroxan series in therapeutics. In particular the invention concerns pharmaceutical compositions containing benzofuroxan derivatives as active ingredients and their use as tolerance resistant nitric oxide donors in treatment of angina pectoris.

2. Description of the Prior Art

After the discovery of endothelium-derived relaxing factor (EDRF) by Furchgott et al (1980), and the elucidation of the biochemistry of EDRF by a number of laboratories (Ignarro, 1989; Vane et al, 1990, Bassenge et al, 1988; and Vanhoutte, 1989) it is now widely accepted that EDRF is the endogenous nitrovasodilator, nitric oxide (NO) donor. The organic nitrates and related compounds owe their pharmacological action to the release of nitric oxide (NO) and these compounds are collectively called nitrovasodilators. NO stimulates the guanylate cyclase enzyme in vascular smooth muscle cells resulting in increased levels of cyclic GMP. This leads to dephosphorylation of myosin light chain which results in relaxation of smooth muscles (Murad 1986). NO is known to be involved in a number of bio-regulatory processes like, vasodilatation, platelet deaggregation, vascular smooth muscle proliferation, etc.

Organic nitrates are used in prophylaxis, treatment and management of patients with angina pectoris. These are also useful in congestive heart failure associated with acute myocardial infarction, hypertension associated with surgical procedures and to produce controlled hypotension during surgical procedures. Among organic nitrates, nitroglycerine (sublingual) which is currently in use, is the drug of choice for immediate relief of anginal symptoms. Prophylactic treatment of stable angina pectoris involves the use of one or more drugs such as long acting nitrates like isosorbide dinitrate, a beta-blocker and/or a calcium channel antagonist, particularly in patients likely to experience coronary spasm. In some cases this triple therapy satisfactorily control angina. They are quite effective in the treatment of these conditions when used intermittently.

Frequently repeated use of nitrates result in decrease in their pharmacological effects, a phenomenon well recognized as nitrate tolerance. The mechanism of tolerance is not well defined As early as 1973, Needleman and Johnson (1973) have reported that tolerance to nitroglycerine could occur in isolated rabbit arteries. It was hypothesized by them that depletion of sulphydryl groups was associated with the development of tolerance to nitroglycerine. This is a major problem in the clinical use of organic nitrates (Frampton et al, 1992). Currently, the development of tolerance is reduced by the use of intermittent dosing schedule with a nitrate-free interval of 10–12 hrs. However, this intermittent use is associated with decreased exercise tolerance during the last part of nitrate-free interval. This suggests possibility of increased frequency of or severity of angina during nitrate-free interval. The importance of development of tolerance has increased as these drugs are used more commonly in various dosage forms like oral, transdermal, and intravenous preparations and even as sustained-release preparations. Several indirect indices like exercise duration, systemic blood pressure, pulmonary artery pressures and pulmonary artery wedge pressure has been used to assess tolerance to organic nitrates. However, it is not clear whether decreased response to nitrates is due to tolerance of the vascular smooth muscle cells or changes in regulatory factors like activation of neurohumoral factors or fluid retention etc. (Armstrong and Moffat, 1983). Irrespective of the mechanisms of tolerance development, clinically it is important to develop nitric oxide donors with least tendency to develop tolerance.

This problem of "tolerance" is still confronting the physicians as is be evident from
(a) The Merck Manual of diagnosis and therapy (16th Edition 1992), pages 498–505,
(b) MARTINDALE, The Extra Pharmacopoea (30th Edition) 1993, pages 1019–1021,
(c) The Essential Guide to Prescription Drugs 1994 edited by James W Long and James J Rybacki, pages 42–46, (d) Harrison's Principles of Internal Medicine (13th Edition 1944) page 1077–1084 and (e) Goodman and Gilman's, The Pharmacological Basis of Therapeutics (9th edition, 1996) pages 759–767.

P B Ghosh et al. (Journal of Medicinal Chemistry, 1968) disclosed the method of synthesis of various benzo-2,1,3-oxadiazoles (benzofurazans) and their N-oxides (benzofuroxans) and their potential as antileukemic and immuno-suppressive drugs in vitro.

P B Ghosh et al. (Journal of Medicinal Chemistry, 1972) tested 4-nitro benzofurazans and 4-nitrobenzofuroxans bearing electron withdrawing substitutents in the 5 and 6 position (relative to $NO_2$) as potential antileukemic and immuno suppressive drugs in vitro.

P B Ghosh et al (Journal of Medicinal Chemistry, 1974) tested benzofuroxan and its derivatives for their vasodilation activities and found flurazanobenzofuroxan, furazobenzothiadiazole and their N-oxides as potent vasodilators.

Nishikawa et al. (The Journal of Pharmacology and Experimental Therapeutics, 1982) disclosed effect of N-ethoxycarbonyl-3-morpholinosydnonimine and its metabolites 3-morpholinosydnonimine, cyanomethyleneamino morpholine, N-nitroso-N-morpholinoamino acetonitrile as novel antianginal agent.

F. Murad (J. Clin. Invest, 1986) disclosed cyclic guanosine monophosphate as a mediator of vasodilation.

James Frampton et al. (Drug Evaluation, Adis International Limited, 1992) gives a review of pharmacology and therapeutic efficiency of nicorandil in angina pectoris. Nicorandil, which has both vasodilator and venodilating properties was found to offer an effective alternative to established vasodilator therapy with conventional nitrates and calcium antagonists in the long term treatment of stable angina pectoris.

U.S. Pat. No. 5,272,164 disclosed novel carboximidamide derivatives particularly N-cyano-$N^1$-substituted pyridine carboximidamide derivatives having vasodilating effect and hypotensive effect besides other physiological effects which are helpful in treatment of ischemic heart diseases.

U.S. Pat. No. 5,424,326 disclosed phenyl-1,2,5-oxadiazole carboxamide-2-oxide and its derivatives, which are useful for the treatment of disorders of the cardiovascular system.

EP-A-0 574726 disclosed fused 1,2,5-ozadiazole-2-oxides i.e. furoxan derivatives their preparation and use as pharmaceutically active compounds including pharmaceutical compositions for treatment of angina pectoris.

F Benedini et. al. (J. Med. Chem. 1995) disclosed a new nitro ester-3-[(nitroxy)alkyl]-2H-1,3-benzoxazin-4(3H)-ones showing marked inhibitory activity against ischemia-induced electrocardiographic changes, with only limited systemic hemodynamic effects. These new nitro ester derivatives, endowed with marked anti-anginal activity, which is not associated with concurrent and pronounced fall in systemic blood pressure, are indicative of a new class of selective nitrovasodilators having a preferential action on large coronary vessels, which could be clinically relevant in the treatment of coronary artery diseases.

However, none of the above prior art disclosures on the drugs specifically used as vasodilator for treatment of cardiac ailments tackles the problem associated with the conventional NO-donors to develop tolerance in the patient after continuous use for a period of time. The present invention evaluates the benzofuroxan derivatives for their NO donor activities particularly with reference to their tendency to develop tolerance for continued application of the drug. Significantly, the invention identifies the molecules showing vasodilator activity without tendency to develop tolerance unlike the conventional nitric-oxide donors.

SUMMARY OF THE INVENTION

The present invention provides, in the first aspect, benzofuroxan derivatives and pharmaceutically acceptable salts thereof, for their use in cardiovascular disorders like coronary heart diseases.

Such salts include, but are not limited to, oxalate, tartarate, maleate, methyl sulphonate, p-toluene sulphonate, etc.

The invention farther provides pharmaceutical formulations comprising benzofuroxan derivatives to be used for treatment of cardiac disorders.

The invention also provides for a method of treatment of mammals including human being of coronary heart diseases by administration of a compound of benzofuroxan series.

DETAILED DESCRIPTION OF THE INVENTION

The compounds of the benzofuroxan series used for cardiovascular disorders are represented by the general formula (I).

(I)

and pharmaceutically acceptable salts thereof wherein:
R is halogen, acetoxy, —X—R', —C(O)NR"R'", or —C(O)Cl;
X is oxygen, sulfur, —C(O)—, or —C(O)O—;
R' is hydrogen, straight chain or branched lower alkyl ($C_1$–$C_8$);
R" and R'" are independently hydrogen, straight chain or branched lower alkyl ($C_1$–$C_8$) or R" and R'" are linked together with or without a heteroatom selected from the group consisting of oxygen and nitrogen wherein substitution on nitrogen is with hydrogen or lower alkyl.

the representative compounds of the invention showing tolerance resistant NO defined above are given in the Table-1.

TABLE 1

| Compound No. | R |
|---|---|
| 1 | —Cl |
| 2 | —S—$CH_2CH_2CH_3$ |
| 3 | —COOH |
| 4 | —$SCH_3$ |
| 5 | —OC(O)—$CH_3$ |
| 6 | —COCl |
| 7 | —CHO |
| 8 | —$COOCH_3$ |
| 9 | —OH.HCl |
| 10 | —$CONH_2$ |
| 11 | —$COOC_2H_5$ |
| 12 | —$COOCH_2$—$CH_2$—$CH_3$ |
| 13 | —$COOCH(CH_3)_2$ |
| 14 | —COO$^t$Bu |
| 15 | —$CON(CH_3)_2$ |
| 16 | substitution (a) |
| 17 | substitution (b) |
| 18 | —$CONHCH(CH_3)_2$ |
| 19 | —CONH$^t$Bu |

(a)

(b)

The alkoxy carbonyl benzofuroxan derivatives of the general formula (I), and their pharmaceutically acceptable salts can be prepared by a process which comprises,
(a) reacting chlorocarbonyl benzofuroxan and an alcohol in solvent such as tetrahydrofuran at room temperature;
(b) adding a base such as triethylamine to the reaction mixture;
(c) refluxing the reaction mixture till the completion of the reaction;
(d) removal of the solvent followed by addition of water and extraction with organic solvent such as ethyl acetate;
(e) concentration of ethyl acetate layer;
(f) purification by column chromatography, and
(g) optionally transforming into the corresponding pharmaceutically acceptable salts.

Said products of steps (f) and (g) are characterized by m.p. and the conventional spectroscopic techniques.

The alkoxy carbonyl benzofuroxan derivatives of the general formula (I), and their pharmaceutically acceptable salts can also be prepared by a process which comprises,
(a) reacting carboxy benzofuroxan with saturated solution of alcoholic HCl;

(b) removal of excess of alcohol under reduced pressure to get the residue;

(c) washing the residue with 0.2 N aq. NaOH solution, extracting with solvent such as ether and concentration of the ether layer, (d) purification by column chromatography, and (e) optionally transforming into the corresponding pharmaceutically acceptable salts.

Said products of steps (d) and (e) are characterized by m.p. and the conventional spectroscopic techniques.

The 5(6)-alkyl mercapto benzofuroxan derivatives of the general formula I, and their pharmaceutically acceptable salts can be prepared by a process which comprises, (a) reacting 2-nitro-4-alkylmercapto aniline with concentrated hydrochloric acid and sodium nitrite, (b) reacting the reaction product of step (a) with sodium azide to obtain 2-nitro-4-alkylmercapto phenyl azide, (c) thermal cyclization of 2-nitro-4-alkylmercapto phenyl azide in a solvent, such as toluene, benzene, or xylene to produce 5(6)-alkylmercapto benzofuroxan, (d) purification by column chromatography, and (e) optionally transforming into the corresponding pharmaceutically acceptable salts.

Said products of steps (d) and (e) are characterized by m.p. and the conventional spectroscopic techniques.

The alkoxy carbonyl benzofuroxan derivatives of general formula I can be further prepared by a process which comprises, (a) reacting carboxy benzofuroxan and an equimolar amount of an alcohol such as methanol, ethanol, isopropanol, tertiary butanol, etc. in methylene chloride, (b) adding 4-dimethylamino pyridine and N,N'-dicyclohexyl carbodiimide under stirring and continuing the stirring for a period of 2 to 16 hours at room temperature, to complete the reaction, (c) filtering the reaction mixture when the filtrate on evaporation under reduced pressure gives the crude product, (d) the product thus obtained is purified by column chromatography, and (e) optionally transforming into the corresponding pharmaceutically acceptable salts.

Said products of steps (d) and (e) are characterised by m.p. and the conventional spectroscopic techniques.

Pharmaceutical Compositions for NO-donor Molecules

The compounds according to this invention as given by general formula (I) or their salts or complexes can be administered orally, intravenously or parenterally as a pharmaceutical preparation in liquid or solid form. It may also be administered via topical, transdermal, sublingual, buccal or rectal route for example as a suppository, ointment, cream, powder, transdermal patch, metered aerosol or spray.

The pharmaceutically acceptable carriers present in the composition of this invention are materials recommended for the purpose of administering the medicament. These may be liquid or solid materials, which are otherwise inert or medically acceptable and are compatible with the active ingredients.

Evaluation of the Biological Activity

Methods a) In Vitro Screening of NO Donors

The method adopted was a modified method of Nishikawa et al (1982). Albino rabbits of either sex were stunned and exsanguinated. Thoracic aorta was quickly removed and cut helically (at an angle of 45°) into strips 4–5 mm wide and 25 to 30 mm long, after removal of adventitial connective tissue. The endothelium was rubbed off gently using a cotton swab soaked in Kreb's solution. Two strips were fixed vertically in organ baths containing 20 ml. Kreb's solution maintained at 37° C. and bubbled with oxygen. A resting tension of 4 g was applied and the preparation was allowed to equilibrate for 30 min. Each preparation was exposed to two primer doses of KCl (30 mM). After the contraction reached a maximum, the bath was drained off and replaced with fresh Kreb's solution. Half an hour later, cumulative dose response curve for the test compound was taken on one tissue (test) and for glyceryl trinitrate (GTN) in the other (standard). The dose range used was from $10^{-9}$ M to $10^{-3}$ M with a contact period of 4 min. for each dose. After the maximum relaxation was achieved with the last dose, papaverine ($10^{-4}$ M) was added to obtain the maximum relaxation.

Tolerance was induced in both the tissues by adding 440 $\mu$M of GTN for 90 minutes. During this period the bath solution was changed every 30 min. and 440 $\mu$M of GTN was replaced. Later both the tissues were washed thoroughly and the dose response curve (DRC) for both the test compound and the standard were repeated. The percentage relaxation with individual doses was calculated by taking the maximum relaxations to $10^{-4}$ M papaverine as 100% relaxation. A graph was plotted by taking the percentage relaxation vs the log (M) concentration of the compounds. The relaxant activity of the test compound was assessed by calculating the mean relative potencies (MRP) and the mean activity ratio (MAR), both before and after tolerance, as defined below:

$$MRP = \frac{\text{Concentration of GTN producing 50\% of its maximum relaxation}}{\text{Concentration of test compound producing 50\% of the maximum relaxation of GTN}}$$

$$MAR = \frac{\text{Maximum relaxation produced by the test compound}}{\text{Maximum relaxation produced by } GTN}$$

Figure 1:
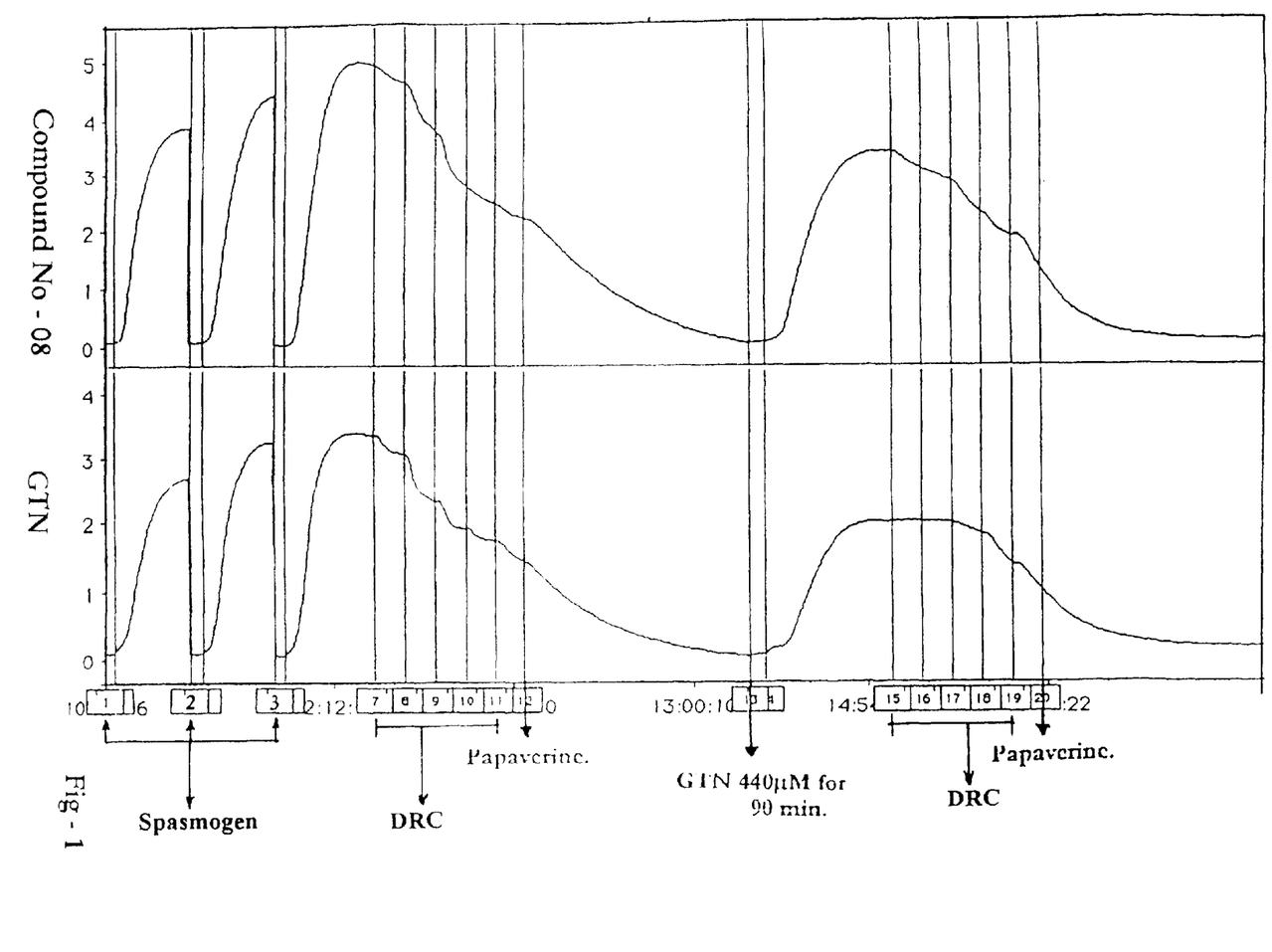
FIG. 1 gives the dose response curve for one of the test compound (compound No.8) and GTN.
Figure 2:
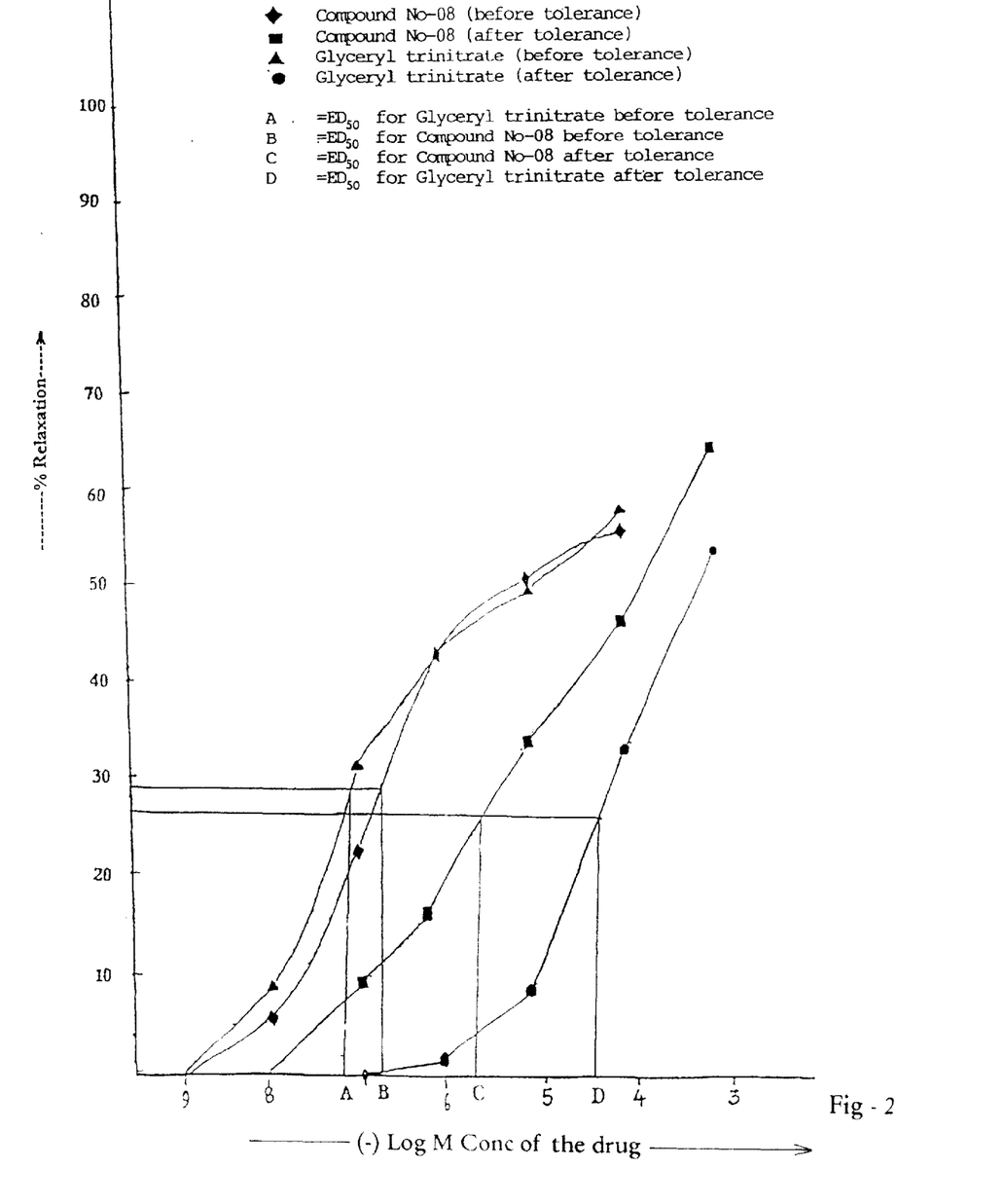
FIG. 2 gives the dose response curves (percentage relaxation vs the log(M) concentration) for GTN and one of the test compounds (Compound No. 8) before and after development of tolerance.

Selection criteria for in vivo study: Compounds having MRP greater than 3 and MAR greater than 1.3 after tolerance were selected for in vivo study. Dose response curve for compound 8 is given in FIGS. 1 and 2 of the accompanying drawings as an example for the estimation of MRP and MAR.

b) In Vivo Pharmacological Screening

A modified method of Benedini et al (1995) was adopted for studying the anti-anginal effect of the chosen compounds. Guinea pigs of either sex, weighing approximately 400–600 g were used for this study. Animals were anesthetized with urethane (1.25 g/kg, i.p.) and jugular vein was cannulated for intravenous administration of drugs/vehicle. Mean arterial blood pressure (MABP) was monitored by a cannula inserted into the right carotid artery and connected to a pressure transducer. Standard limb lead II electrocardiogram was recorded continuously. All the recordings were carried out on a MacLab system (AD Instruments, UK).

The ability of the test compounds to suppress the vasopressin induced T-wave elevation was used as the model for studying the anti-anginal effects of the compounds. Guinea pigs were divided into two groups for the purpose of this study, i) control group (pretreated with the vehicle for the compound) and ii) drug treated group.

i) Control Group

In this group of animals the solvent used for dissolving the test compound was administered intravenously in a volume of 1 ml/kg. The basal T-wave heights, heart rates and MABP and changes after vehicle administration were noted. Thirty seconds later 1 I.U./ml/kg of vasopressin was administered intravenously. The T-wave heights, heart rates and MABP and their changes after vasopressin administration were also noted. The T-wave elevation (after vasopressin administration), maximum rise in MABP, and changes in heart rate were calculated from the above data and expressed as mean±standard deviation.

ii) Drug Treated Group

The effects of the test compound in suppressing the T-wave elevation caused by vasopressin were evaluated with atleast three dose levels. Groups of 6 guinea pigs were used for each dose. The test compound was injected 30 seconds prior to vasopressin administration. Changes in MABP, heart rate and T-waves were recorded as described for the control group. The percentage inhibition of vasopressin induced T-wave elevation was calculated for each dose taking the T-wave height estimated in control group as 100%. From the dose vs percent inhibition relationship, the dose required for 50% inhibition ($ED_{50}$) for the T-wave elevation was estimated.

Determination of the $ED_{20}$ Values for Drop in MABP

In a separate group of animals the drop in MABP after administration of the test compound (dose range of 0.1–1000 μg/kg, i.v.) was studied. Atleast three animals were used for each dose. Care was taken so that the doses were given only after the MABP had stabilized from the effects of the previous dose. All doses were injected in a final volume of 1 ml/kg. The drop in MABP was noted for increasing concentrations of the test compound and a dose response curve was drawn. From this graph the dose required to produce a 20% fall in MABP ($ED_{20}$) was calculated. The specificity of the test compound was defined by the selectivity index, which was calculated as shown below.

$$\text{Selectivity Index} = \frac{\text{Dose required for 20\% reduction in } MABP \, (\mu g/\text{kg})}{\text{Dose required for 50\% inhibition of } T\text{-}wave \text{ elevation} \, (\mu g/\text{kg})}$$

Compounds having selectivity ratio greater than 30 times that of GTN were selected for initial toxicology evaluation. The selectivity index for GTN was estimated to be 0.017.

Results of in Vitro Screening of NO Donors

The results of in vitro screening of the NO donors are given in the following Table 2.

Results of in Vivo Evaluation

The compounds, which were selected based on in-vitro studies, were subjected to in-vivo studies to assess their anti-anginal action. Compounds with sufficient selectivity (i.e. lower hypotension) and anti-anginal action are listed in Table-3.

TABLE 3

In vivo activity of selected Nitric Oxide donors

| Compound No. | Dose required for 20% fall in B.P. ($ED_{20}$ μg/kg,) (A) | Dose required for 50% inhibition of T-wave ($ED_{50}$ μg/kg,) (B) | Selectivity Index (A/B) (C) |
|---|---|---|---|
| GTN | 8.22 | 474.40 | 0.017 |
| 6 | 383.19 | 170.70 | 2.25 |
| 8 | 539.06 | 93.75 | 5.75 |
| 12 | 248.86 | 681.68 | 0.37 |
| 13 | 318.55 | 113.16 | 2.81 |

It was observed that compounds 6, 8, 12 and 13 have a high selectivity index as compared to GTN. In the case of compounds 6, 8 and 13, the index is significantly higher. The index showed that these compounds could elicit anti-anginal activity at a dose, which had minimum systemic effects. Their selectivity in dilating the coronary arteries was quite high as compared to a conventional drug like GTN.

The high selectivity index of these compounds as compared to nitroglycerine show that they selectively dilate the coronary arteries and have a lower tendency to cause hypotension during clinical usage. For example, the compound with lowest selectivity index, (compound 12), is 22 times more selective as compared to GTN. This shows that these compounds have very little tendency to cause hypotension. Conventional nitrates like GTN cause tachycardia, retrosternal discomfort, palpitations, collapse, syncope and

TABLE 2

In vitro activity of NO donors

| Compound No. | Mean Relative Potency before tolerance | Mean Relative Potency after tolerance | Mean Activity Ratio before tolerance | Mean Activity Ratio after tolerance |
|---|---|---|---|---|
| 1. | 0.03 | 1.2 | 0.7 | 1.3 |
| 2. | 1.7 | 2.9 | 1.0 | 1.3 |
| 3. | Low Potency | Low Potency | 0.5 | 0.2 |
| 4. | Low Potency | Low Potency | 1.3 | 1.2 |
| 5. | Low Potency | Low Potency | 0.7 | 0.4 |
| 6. | 0.8 | 3.4 | 1.3 | 1.5 |
| 7. | 0.17 | 0.54 | 1.05 | 1.5 |
| 8. | 0.18 | 7.99 | 1.44 | 1.36 |
| 9. | Low Potency | Low Potency | 0.32 | 0.52 |
| 10. | 0.08 | 1.6 | 1.2 | 1.25 |
| 11. | 0.79 | 16.36 | 1.17 | 1.72 |
| 12. | 0.44 | 9.0 | 1.06 | 1.6 |
| 13. | 0.4 | 10.6 | 1.1 | 1.6 |
| 14. | 0.71 | 11.5 | 1.1 | 1.25 |
| 15. | 0.028 | 2.73 | 0.92 | 0.88 |
| 16. | 0.06 | 0.46 | 1.07 | 0.92 |
| 17. | 0.017 | 0.85 | 0.75 | 0.85 |
| 18. | 0.046 | 3.79 | 0.82 | 1.43 |
| 19. | 0.06 | 9.28 | 1.03 | 2.07 | postural hypotension, etc. as a manifestation of hypotensive effect. This could limit its use in selected patients. However, the compounds described in this invention due to a lower tendency to cause hypotension are superior to conventional nitrates.

The benzofuroxans described in this invention can be used in cardiovascular disorders like acute effort angina, angina prophylaxis, mixed angina and silent ischemia, acute myocardial infarction, congestive heart failure, etc. They can be used alone or in combination with beta adrenergic blockers like propranolol, atenolol, carvedilol, etc. and calcium channel antagonists like verapamil, diltiazem, etc.

The method of preparation of the representative compounds for use in treatment of cardiac disorders according to this invention are given in the following examples:

EXAMPLE 1

Preparation of 5(6)-n-propylmercapto benzofuroxan. (Compound 2)

In a 250 ml round bottom flask, was added 10.0 g of 2-nitro-4-thiopropylaniline. To it was added 50 ml of D.M. water and 40 ml concentrated HCl. It was stirred at 0–10° C. for 1 hour. Then at 0° C., a solution of 4.7 g of sodium nitrite in 10 ml water was added. After 10 minutes 4.5 g of sodium azide in 10 ml water was added to obtain 6.2 g of 2-nitro-4-thiopropyl phenyl azide as a yellow solid.

12 ml of dry toluene, was charged with 2.0 g of 2-nitro-4-thiopropyl phenyl azide. The dark brown solution which was formed was stirred at 80° C. for 4 hours. The solvent was removed under vacuum to give a brown solid, which was further charcoalized in ethanol:water (7:3) and filtered to give 800 mg of 5(6)-n-propyl mercapto benzofuroxan.

IR(KBr): 3092, 2967, 1605, 1517, 1456, 1293, 1125, 1090 $cm^{-1}$

PMR ($CDCl_3$) δ: 6.8–7.5 (3H,m), 3.0 (2H,t), 1.8 (2H,m), 1.1 (3H,t)

Mass: 210 ($M^+$), 150 ($M^+$-$N_2O_2$)

EXAMPLE 2

Preparation of 5(6)-methylmercapto benzofuroxan. (Compound 4)

To a stirred mixture of 2 g of 4-thiocyanato-2-nitroaniline in 20 ml methanol was added a solution of 1.2 g potassium hydroxide in 10 ml methanol. The solution became dark. The mixture was stirred at 20° C. for 2 hours. Then 1 g of methyl iodide was added when a clear solution was obtained in 2 minutes and it was stirred at 20° C. for 1 hour. Methanol was removed on a rotary evaporator at 40° C. Then 50 ml of water was added to the residue and the product was extracted with ethyl acetate. The organic extracts were combined and dried over anhydrous $Na_2SO_4$. Ethyl acetate was removed on a rotary evaporator when 1.2 g of 4-methylmercapto-2-nitroaniline was obtained, which was used for the next step without further purification.

To a stirred mixture of 0.75 g 4-methylmercapto-2-nitroaniline and 5 ml concentrated HCl was added 20 ml of water, and stirring was continued for another 5 minutes. The mixture was cooled to 0° C. and then a solution of 1 g of sodium nitrite in 5 ml water was added and stirred at 0° C. for 2 hours. It was then filtered rapidly under suction and the filtrate was collected. To the filtrate was added a solution of 1.5 g of sodium azide in 5 ml water when a solid was precipitated with frothing. The solid was extracted with methylene chloride (50 ml×2). The combined organic extracts were dried over anhydrous $Na_2SO_4$. The solvent was evaporated on a rotary evaporator when 0.5 g of 4-methylmercapto-2-nitrophenyl azide was obtained. The solid was used for the next step without further purification.

A mixture of 0.5 g 4-methylmercapto-2-nitrophenyl azide and 10 ml toluene was heated with stirring at 100° C. for 2 hours. Toluene was removed under vacuum at 60° C. and recrystallization was carried out with hexane:ethylacetate (5:7) when 0.41 g of 5(6)-methylmercapto benzofuroxan was obtained.

m.p.: 114° C.

IR (KBr): 2920, 1600, 1515, 1460 $cm^{-1}$

EXAMPLE 3

Preparation of 5(6)-n-propoxy carbonyl benzofuroxan (Compound 12)

5(6)-Carboxy benzofuroxan (2.0 g, 0.11 mole) was refluxed in a saturated solution of n-propionolic HCl for 16 hours. n-Propanol was removed under vacuum and the residue was redissolved in diethyl ether (150 ml). The solution was then washed with aqueous NaOH (50 ml, 0.1 mole), followed by water (100 ml) and dried over $Na_2SO_4$ Ether was removed under vacuum to give an oil which was purified by column chromatography.

Yield: 1.0 g, (45%)

m.p.: 30–32° C.

IR (KBr): 1725, 1613, 1585, 1540, 1490 $cm^{-1}$

P.M.R. (200 MHz, $CDCl_3$) δ: 1.09–1.08 (2H,t,J=7.4 Hz), 1.58–2.17(2H,m), 4.30–4.36 (3H,t,J=6.6 Hz), 7.36–7.86 (3H,m).

Mass: 222($M^+$), 180, 163, 75.

Alternatively, compound 12 can also be prepared by the following procedure:

5(6)-Chlorocarbonyl benzofuroxan (100 mg) and n-propyl alcohol (150 mg) were dissolved in THF (10 ml) at room temperature. To the reaction mixture triethylamine (0.1 ml) was added and reaction mixture was refluxed for 24 hrs. THF was removed under reduced pressure. To the residue 10 ml water was added and extracted with ethyl acetate (3×20 ml). Ethyl acetate was removed under reduced pressure to get sticky mass which was purified by column chromatography using ethylacetate: hexane (1:9) to give 65 mg of compound 12.

Compound 12 can also be prepared by the method of preparation of compound 13.

EXAMPLE 4

Preparation of 5(6)-isopropoxy carbonyl benzofuroxan. (Compound 13)

To a solution of 5(6)-carboxy benzofuroxan (1.0 g, 0.0055 mole) and isopropyl alcohol (0.9 ml., 0.01 mole) in $CH_2Cl_2$ (50 ml) were added 4-dimethylamino pyridine (70 mg) and N,N'-dicyclohexyl carbodiimide (2.28 g, 0.011 mole) under stirring. The reaction mixture was stirred for 2 hours at room temperature. It was filtered and the filtrate on evaporation under reduced pressure gave crude product, which was purified by column chromatography (n-hexane) to give the title compound as yellow solid (0.7 g, 57%).

m.p.: 65–67° C.

IR (KBr): 1716, 1622, 1585, 1537 $cm^{-1}$

PMR (200 MHz, $CDCl_3$) δ: 1.3–1.41 (6H,d,J=6.2 Hz), 5.15–5.37 (1H,m), 7.51–8.21 (3H,m),

Mass: 222 (M+), 180, 163, 103, 75.

Compound 13 can also be prepared by the method of preparation of compound 12.

Oral Formulations

Orally they may be administered as solid dosage forms for example as pellets, granules, powder, sachet or as discreet units such as tablets or capsules, etc. Other orally administered pharmaceutical preparations include monophasic and biphasic liquid dosage forms either in ready to use form, or forms suitable for reconstitution such as mixtures, syrups, suspensions or emulsions. The preparations in addition may contain diluents, dispersing agents, buffers, stabilizers, solubilizers, surface active agents, preservatives, chelating agents and/or other pharmaceutical additives. Aqueous or non aqueous vehicles or their combination may be used and if desired may contain suitable sweeteners, flavouring agents or similar substances. In the case of a suspension or emulsion a suitable thickening agent, suspending agent or emulsifying agent may be present. Pharmaceutical preparations can have a slow, delayed or controlled release of active ingredients as is provided by a matrix or diffusion controlled system.

Parenteral Formulations

For parenteral administration, the compounds or their salts or suitable complexes may be presented in a sterile vehicle which may be an aqueous or non aqueous vehicle or a combination thereof The examples of vehicles are water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc. Some suitable additives are for example tartrate, citrate, or similar buffers, alcohols, sodium chloride, dextrose and high molecular weight liquid polymers. Another alternative is sterile powder for reconstitution. The compound may be administered in the form of injection, intravenous infusion/drip, or suitable depot preparation.

When the present invention, its salts or a suitable complex is presented as a discrete unit dosage form like a tablet, it may contain in addition medically inert excipients as are used in art. Diluents such as starch, lactose dicalcium phosphate, lubricants or similar additives like talc, magnesium stearate, polymeric substances like methyl cellulose, hydroxy propyl cellulose, fatty acids and derivatives, sodium starch glycollate, etc. can also be used.

EXAMPLE 5

Preparation of Oral Dosage Form of the Benzofuroxan Derivatives Given in Table 1.

The compounds described in Table 1 can be prepared in the form of tablets, containing the active ingredient in the range of 0.03 to 3 mg per tablet. A typical tablet has the following composition:

| Active ingredient | as given above |
|---|---|
| Starch | 27 mg |
| Lactose | 70 mg |
| Polyvinyl pyrolidone (k-30) | 1.0 mg |
| Talc | 1.5 mg |
| Magnesium stearate | 0.5 mg |

EXAMPLE 6

Preparation of Parenteral Dosage Form of Benzofuroxan Derivatives Given in Table 1

A preparation suitable for parenteral administration has the following composition:

| Active ingredient | 1 mg. |
|---|---|
| Poly ethylene glycol - 400 | 0.5 ml |
| Isotonic saline solution q.s. or water for injection | 1 ml |

These examples are presented by way of illustration alone and in no way limit the scope of the invention.

I claim:

1. A pharmaceutical composition for treating cardiovascular disorders containing a pharmaceutically active amount of a benzofuroxan compound represented by the general formula (I)

and pharmaceutically acceptable salts thereof, said pharmaceutical composition further containing a pharmaceutically acceptable carrier, wherein:

R is halogen, acetoxy, —X—R', —C(O)NR"R'", or —C(O)Cl;

X is oxygen, sulfur, —C(O)—, or —C(O)O—;

R' is hydrogen, straight chain or branched lower alkyl ($C_1$–$C_8$);

R" and R'" are independently hydrogen, straight chain or branched lower alkyl ($C_1$–$C_8$) or R" and R'" are linked together with or without a heteroatom selected from the group consisting of oxygen and nitrogen wherein substitution on nitrogen is with hydrogen or lower alkyl.

2. The pharmaceutical composition as claimed in claim 1, wherein the substituent R is in 5(6) position.

3. The pharmaceutical composition as claimed in claim 1, wherein the compound represented by the general formula (I) is a tolerance resistant antianginal compound.

4. The pharmaceutical composition as claimed in claim 2, wherein the compound represented by the general formula (I) is a tolerance resistant anti-anginal compound.

5. The pharmaceutical composition as claimed in claim 4, wherein said compound of formula (I) is selected from the group consisting of:

(a) 5(6)-isopropoxycarbonyl benzofuroxan,
(b) 5(6)-n-propoxycarbonyl benzofuroxan,
(c) 5(6)-methoxycarbonyl benzofuroxan,
(d) 5(6)-chlorocarbonyl benzofuroxan,
(e) 5(6)-tertiarybutyl amino carbonyl benzofuroxan,
(f) 5(6)-ethoxy carbonyl benzofuroxan,
(g) 5(6)-formyl benzofuroxan,
(h) 5(6)-isopropylamino carbonyl benzofuroxan,
(i) 5(6)-n-propylmercapto benzofuroxan,
(j) 5(6)-chloro benzofuroxan,
(k) 5(6)-tertiary butoxy carbonyl benzofuroxan,
(l) 5(6)-amino carbonyl benzofuroxan,
(m) 5(6)-morpholino carbonyl benzofuroxan,
(n) 5(6)-dimethylamino carbonyl benzofuroxan and
(o) 5(6)-((4-methyl)piperazine-1-yl)carbonyl benzofuroxan.

6. The pharmaceutical composition as claimed in claim 1, in the form of an oral formulation.

7. The pharmaceutical composition as claimed in claim 1, wherein said pharmaceutically acceptable carrier is selected from the group consisting of starch, lactose, polyvinyl pyrolidone (k-30), talc and magnesium stearate.

8. The pharmaceutical composition as claimed in claim 1, in the form of a parenteral formulation.

9. The pharmaceutical composition as claimed in claim 1, wherein said compound of formula (I) is selected from the group consisting of:
 (a) 5(6)-isopropoxycarbonyl benzofuroxan,
 (b) 5(6)-n-propoxycarbonyl benzofuroxan,
 (c) 5(6)-methoxycarbonyl benzofuroxan,
 (d) 5(6)-chlorocarbonyl benzofuroxan,
 (e) 5(6)-tertiarybutyl amino carbonyl benzofuroxan,
 (f) 5(6)-ethoxycarbonyl benzofuroxan,
 (g) 5(6)-formyl benzofuroxan,
 (h) 5(6)-isopropylamino carbonyl benzofuroxan,
 (i) 5(6)-n-propylmercapto benzofuroxan,
 (j) 5(6)-chloro benzofuroxan,
 (k) 5(6)-tertiarybutoxy carbonyl benzofuroxan,
 (l) 5(6)-aminocarbonyl benzofuroxan,
 (m) 5(6)-methylmercapto benzofuroxan,
 (n) 5(6)-morpholino carbonyl benzofuroxan,
 (o) 5(6)-dimethylamino carbonyl benzofuroxan,
 (p) 5(6)-[(4-methyl)piperazine-1-yl]carbonyl benzofuroxan,
 (q) 5(6)-hydroxy benzofuroxan hydrochloride,
 (r) 5(6)-acetoxy benzofuroxan and
 (s) 5(6)-carboxy benzofuroxan.

10. The pharmaceutical composition as claimed in claim 6, wherein said compound of formula (I) is selected from the group consisting of:
 (a) 5(6)-isopropoxycarbonyl benzofuroxan,
 (b) 5(6)-n-propoxycarbonyl benzofuroxan,
 (c) 5(6)-methoxycarbonyl benzofuroxan,
 (d) 5(6)-chlorocarbonyl benzofuroxan,
 (e) 5(6)-tertiarybutyl amino carbonyl benzofuroxan,
 (f) 5(6)-ethoxycarbonyl benzofuroxan,
 (g) 5(6)-formyl benzofuroxan,
 (h) 5(6)-isopropylamino carbonyl benzofuroxan,
 (i) 5(6)-n-propylmercapto benzofuroxan,
 (j) 5(6)-chloro benzofuroxan,
 (k) 5(6)-tertiarybutoxy carbonyl benzofuroxan,
 (l) 5(6)-aminocarbonyl benzofuroxan,
 (m) 5(6)-methylmercapto benzofuroxan,
 (n) 5(6)-morpholino carbonyl benzofuroxan,
 (o) 5(6)-dimethylamino carbonyl benzofuroxan,
 (p) 5(6)-[(4-methyl)piperazine-1-yl]carbonyl benzofuroxan,
 (q) 5(6)-hydroxy benzofuroxan hydrochloride,
 (r) 5(6)-acetoxy benzofuroxan and
 (s) 5(6)-carboxy benzofuroxan.

11. The pharmaceutical composition as claimed in claim 7, wherein said compound of formula (I) is selected from the group consisting of:
 (a) 5(6)-isopropoxycarbonyl benzofuroxan,
 (b) 5(6)-n-propoxycarbonyl benzofuroxan,
 (c) 5(6)-methoxycarbonyl benzofuroxan,
 (d) 5(6)-chlorocarbonyl benzofuroxan,
 (e) 5(6)-tertiarybutyl amino carbonyl benzofuroxan,
 (f) 5(6)-ethoxycarbonyl benzofuroxan,
 (g) 5(6)-formyl benzofuroxan,
 (h) 5(6)-isopropylamino carbonyl benzofuroxan,
 (i) 5(6)-n-propylmercapto benzofuroxan,
 (j) 5(6)-chloro benzofuroxan,
 (k) 5(6)-tertiarybutoxy carbonyl benzofuroxan,
 (l) 5(6)-aminocarbonyl benzofuroxan,
 (m) 5(6)-methylmercapto benzofuroxan,
 (n) 5(6)-morpholino carbonyl benzofuroxan,
 (o) 5(6)-dimethylamino carbonyl benzofuroxan,
 (p) 5(6)-[(4-methyl)piperazine-1-yl]carbonyl benzofuroxan,
 (q) 5(6)-hydroxy benzofuroxan hydrochloride,
 (r) 5(6)-acetoxy benzofuroxan and
 (s) 5(6)-carboxy benzofuroxan.

12. The pharmaceutical composition as claimed in claim 8, wherein said compound of formula (I) is selected from the group consisting of:
 (a) 5(6)-isopropoxycarbonyl benzofuroxan,
 (b) 5(6)-n-propoxycarbonyl benzofuroxan,
 (c) 5(6)-methoxycarbonyl benzofuroxan,
 (d) 5(6)-chlorocarbonyl benzofuroxan,
 (e) 5(6)-tertiarybutyl amino carbonyl benzofuroxan,
 (f) 5(6)-ethoxycarbonyl benzofuroxan,
 (g) 5(6)-formyl benzofuroxan,
 (h) 5(6)-isopropylamino carbonyl benzofuroxan,
 (i) 5(6)-n-propylmercapto benzofuroxan,
 (j) 5(6)-chloro benzofuroxan,
 (k) 5(6)-tertiarybutoxy carbonyl benzofuroxan,
 (l) 5(6)-aminocarbonyl benzofuroxan,
 (m) 5(6)-methylmercapto benzofuroxan,
 (n) 5(6)-morpholino carbonyl benzofuroxan,
 (o) 5(6)-dimethylamino carbonyl benzofuroxan,
 (p) 5(6)-[(4-methyl)piperazine-1-yl]carbonyl benzofuroxan,
 (q) 5(6)-hydroxy benzofuroxan hydrochloride,
 (r) 5(6)-acetoxy benzofuroxan and
 (s) 5(6)-carboxy benzofuroxan.

13. A process for the preparation of a parenteral formulation as claimed in claim 8, which comprises dissolving the active ingredient of general formula (I) or pharmaceutically acceptable salt thereof in polyethylene glycol 400 and diluting the solution so obtained, with an isotonic solution or water to a desired concentration.

14. A method of treating coronary heart disease in mammals which comprises administering to a mammal in need of such treatment a dosage effective amount of a benzofuroxan compound represented by the general formula (I)

(I)

and pharmaceutically acceptable salts thereof, wherein:
R is halogen, acetoxy, —X—R', —C(O)NR"R'", or —C(O)Cl;
X is oxygen, sulfur, —C(O)—, or —C(O)O—;
R' is hydrogen, straight chain or branched lower alkyl ($C_1$–$C_8$);
R" and R'" are independently hydrogen, straight chain or branched lower alkyl ($C_1$–$C_8$) or R" and R'" are linked together with or without a heteroatom selected from the group consisting of oxygen and nitrogen wherein substitution on nitrogen is with hydrogen or lower alkyl.

15. The method as claimed in claim 14, wherein said compound represented by the general formula (I) is a tolerance resistant anti-anginal compound.

16. The method as claimed in claim 15, wherein said compound of formula (I) is selected from the group consisting of
(a) 5(6)-isopropoxycarbonyl benzofuroxan,
(b) 5(6)-n-propoxycarbonyl benzofuroxan,
(c) 5(6)-methoxycarbonyl benzofuroxan,
(d) 5(6)-chlorocarbonyl benzofuroxan,
(e) 5(6)-tertiarybutyl amino carbonyl benzofuroxan,
(f) 5(6)-ethoxycarbonyl benzofuroxan,
(g) 5(6)-formyl benzofuroxan,
(h) 5(6)-isopropylamino carbonyl benzofuroxan,
(i) 5(6)-n-propylmercapto benzofuroxan,
(j) 5(6)-chloro benzofuroxan,
(k) 5(6)-tertiarybutoxy carbonyl benzofuroxan,
(l) 5(6)-aminocarbonyl benzofuroxan,
(m) 5(6)-methylmercapto benzofuroxan,
(n) 5(6)-morpholino carbonyl benzofuroxan,
(o) 5(6)-dimethylamino carbonyl benzofuroxan,
(p) 5(6)-[(4-methyl)piperazine-1-yl]carbonyl benzofuroxan,
(q) 5(6)-hydroxy benzofuroxan hydrochloride,
(r) 5(6)-acetoxy benzofuroxan and
(s) 5(6)-carboxy benzofuroxan.

17. The method as claimed in claim 14, wherein the substituent R is in 5(6) position.

18. The method as claimed in claim 14, which comprises treating angina.

19. The method as claimed in claim 18, wherein said compound of formula (I) is selected from the group consisting of:
(a) 5(6)-isopropoxycarbonyl benzofuroxan,
(b) 5(6)-n-propoxycarbonyl benzofuroxan,
(c) 5(6)-methoxycarbonyl benzofuroxan,
(d) 5(6)-chlorocarbonyl benzofuroxan,
(e) 5(6)-tertiarybutyl amino carbonyl benzofuroxan,
(f) 5(6)-ethoxy carbonyl benzofuroxan,
(g) 5(6)-formyl benzofuroxan,
(h) 5(6)-isopropylamino carbonyl benzofuroxan,
(i) 5(6)-n-propylmercapto benzofuroxan,
(j) 5(6)-chloro benzofuroxan,
(k) 5(6)-tertiary butoxy carbonyl benzofuroxan,
(l) 5(6)-amino carbonyl benzofuroxan,
(m) 5(6)-morpholino carbonyl benzofuroxan,
(n) 5(6)-dimethylamino carbonyl benzofuroxan and
(o) 5(6)-((4-methyl)piperazine-1-yl)carbonyl benzofuroxan.

* * * * *